United States Patent [19]
Manolidis

[11] Patent Number: 6,060,641
[45] Date of Patent: May 9, 2000

[54] MODULAR MANDIBULAR PROSTHESIS

[75] Inventor: Spiros Manolidis, Houston, Tex.

[73] Assignee: Baylor College of Medicine, Hosuton, Tex.

[21] Appl. No.: 09/079,035

[22] Filed: May 14, 1998

[51] Int. Cl.[7] .................................................. A61F 2/30
[52] U.S. Cl. .............................................. 623/16; 623/18
[58] Field of Search ................................. 623/11, 16, 18

[56]  References Cited

U.S. PATENT DOCUMENTS

| | | |
|---|---|---|
| 3,488,779 | 1/1970 | Christensen . |
| 3,720,959 | 3/1973 | Hahn . |
| 4,693,722 | 9/1987 | Wall ......................................... 623/18 |
| 4,726,808 | 2/1988 | Collins . |
| 4,917,701 | 4/1990 | Morgan ..................................... 623/16 |
| 5,002,574 | 3/1991 | May et al. ................................ 623/16 |
| 5,087,259 | 2/1992 | Krenkel .................................... 623/16 |
| 5,445,650 | 8/1995 | Nealis . |
| 5,484,439 | 1/1996 | Olson et al. .............................. 623/16 |
| 5,489,305 | 2/1996 | Morgan . |
| 5,496,371 | 3/1996 | Eppley et al. . |
| 5,554,194 | 9/1996 | Sanders . |

OTHER PUBLICATIONS

Titanium–Coated Hollow Screw and Reconstruction Plate System for Bridging of Lower Jaw Defects: Biomechanical Aspects; Sutter, et al; J. Oral Maxillofac. Surg. 1988; 17; pp. 267–274.

Advantages of Mandibular Reconstruction With the Titanium Hollow Screw Osseointegrating Reconstruction Plate (THORP); Koch, et al; Larynogoscope 104; May 1994; pp. 545–552.

Titanium–Coated Hollow Screw and Reconstruction Plate System (THORP) in Mandibular Reconstruction; Hellem, et al; J. Cranio–Max. Fac. Surg. 16 (1988); pp. 173–183.

The Titanium Hollow–Screw Reconstruction Plate System (THORP); Raveh, et al; Rigid Fixation of the Craniomaxillofacial Skeleton; pp. 620–636.

Titanium Locking Screw Mandibular Reconstruction Plating System; Raveh; Leibinger GmbH 1995.

The Locking Screw Mandibular Reconstruction Plating System; Raveh; Scientific Documentation Research/Development.

Reconstruction of the Lower Jaw Using the THRP System; Raveh, et al; pp. 546–558.

Bridging of Mandibular Defects With Two Different Reconstruction Systems: An Experimental Study; Soderholm, et al; Scientific Article; J. Oral Maxillofac. Surg. 49; pp. 1098–1105, 1991.

(List continued on next page.)

*Primary Examiner*—Paul J. Hirsch
*Attorney, Agent, or Firm*—Tobor, Goldstein & Healey, L.L.P.

[57] ABSTRACT

The invention relates to a modular mandibular prosthesis for use after the resection of a patient's mandible. The modular mandibular prosthesis includes a pair of anchor plates and at least one connector member. Each anchor plate has first and second ends. The second end of each anchor plate is adapted to be attached to a portion of the patient's mandible. At least one connector member is disposed between the pair of anchor plates. Each connector member includes first and second ends. The first end of a connector member is connected to the first end of an anchor plate thereby defining a connection. The second end of a connector member is connected to the first end of the other anchor plate. Additional connector members may be disposed between the anchor plates wherein the first end of the additional connector member is attached to the second end of an adjacent connector member thereby defining a connection and the second end of the additional connector member is connected to the first end of an adjacent connector member thereby defining a connection. Each connection defines a swivel coupling which permits three dimensional movement at each connection thereby facilitating orientation and installation of the modular mandibular prosthesis.

23 Claims, 4 Drawing Sheets

OTHER PUBLICATIONS

The Lingual Application of a Reconstruction Plate: A New Method in Bridging Lower Jaw Defects; Raveh, et al; Technical Notes; J. Oral Maxillofac. Surg. 43; pp. 735–739, 1985.

Surgical Procedures for Reconstruction of the Lower Jaw Using the Titanium–Coated Hollow–Screw Reconstruction Plate System: Bridging of Defects; Raveh, et al; The Otolaryngologic Clinics of North America—vol. 20, No. 3, Aug. 1987; pp. 535–545.

Mandibular Reconstruction with the Titanium Hollow Screw Reconstruction Plate (THORP) System: Evaluation of 62 Cases; Vuillemin, et al; Plastic and Reconstructive Surgery, Vol. 82, No. 5, Nov., 1988; pp. 804–814.

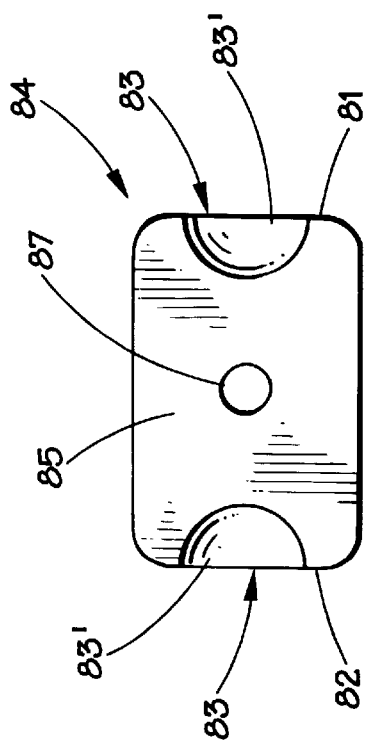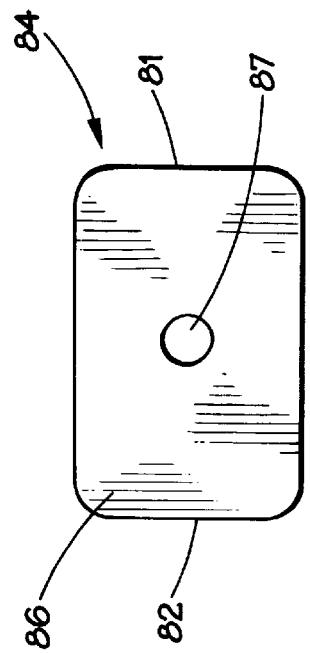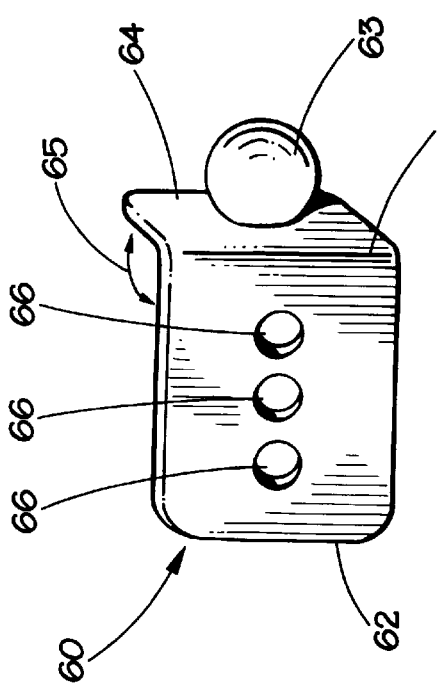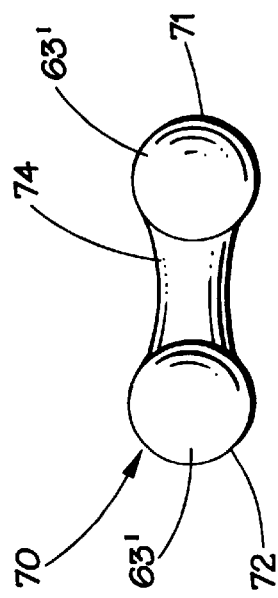

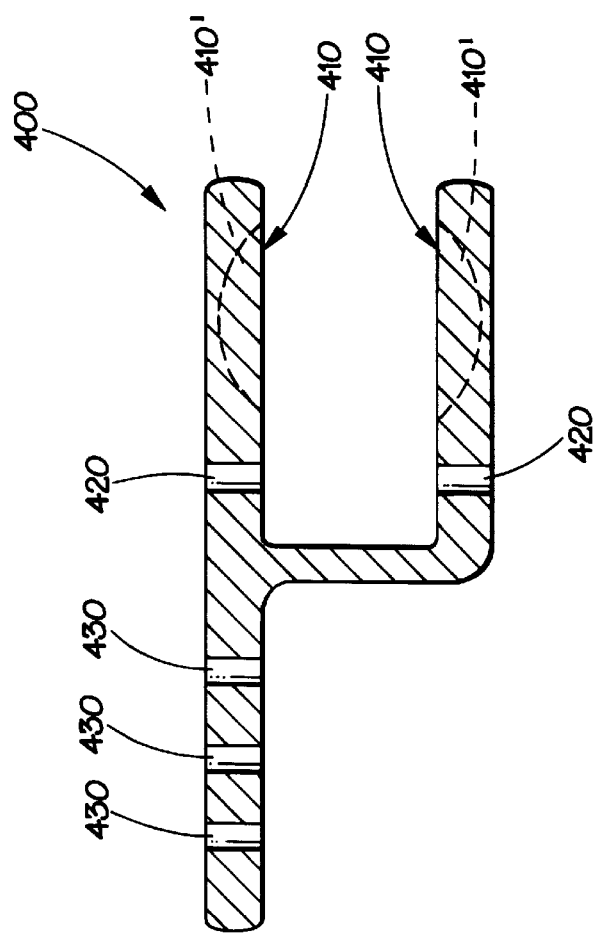
FIG. 9
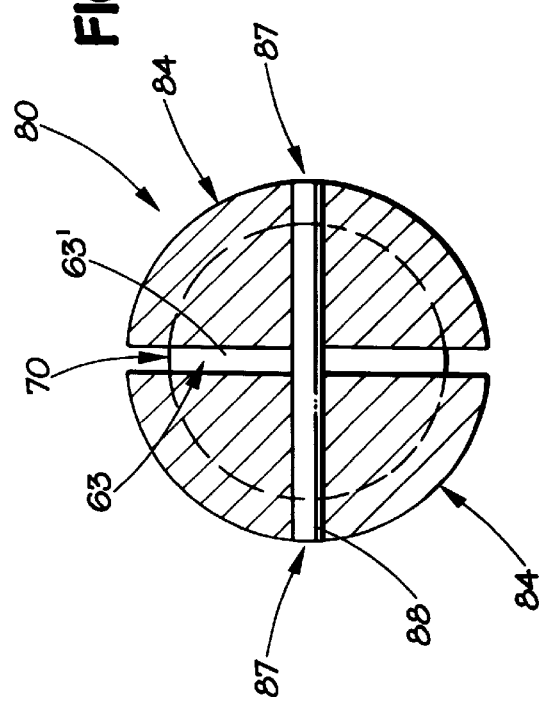
FIG. 7
FIG. 8 ated portion of the mandible. Proper reconstruction of the mandible includes providing the patient with a natural appearance and proper occlusion of the teeth of the mandible with the teeth of the maxilla, or upper jawbone. It is also desirable to enhance the physician's reconstruction of the mandible using a prosthesis which is easy to install and customize, thereby decreasing the length of time the patient is in surgery.

MODULAR MANDIBULAR PROSTHESIS

BACKGROUND OF THE INVENTION

1. Field of the Invention

This invention relates to a modular mandibular prosthesis for replacing a patient's mandible, which has been surgically removed, by forming an artificial mandible or part thereof.

2. Description of Related Art

Mandibular resection, or removal, due to disease has presented physicians with numerous difficulties in reconstructing the mandible, or lower jaw, to give the patient use of his remaining portion of mandible. Proper reconstruction of the mandible includes providing the patient with a natural appearance and proper occlusion of the teeth of the mandible with the teeth of the maxilla, or upper jawbone. It is also desirable to enhance the physician's reconstruction of the mandible using a prosthesis which is easy to install and customize, thereby decreasing the length of time the patient is in surgery.

Prior approaches to replace the portion of the mandible which has been removed include implanting a mandibular prosthesis made out of a plastic, such as an acrylic plastic material, or some other suitable metallic material, such as titanium. The mandibular prosthesis may be attached to the remaining portion of the mandible using various techniques. In one approach, the prosthesis is attached to the mandible using a male coupler and a female coupler which are interlocked with one another. In another approach, a titanium plate is preformed, or bent, to the approximate shape desired to secure the prosthesis across the gap in the mandible created by the resection. In still another approach, the prosthesis is constructed out of mesh and tubular components attached to the mandible. All of these approachs have deficiencies. Most notably, all of these approachs require increased planning time because the prosthesis must be preformed, or molded, prior to surgery. Prior to the operation, the physician approximates the contour of the mandible and approachs to anticipate the shape the mandibular prosthesis must take to function properly. Accordingly, precise calculations and adjustments must be made to the mandibular prosthesis prior to beginning the operation. Should the pre-operation steps of shaping the mandibular prosthesis not be correct, the mandibular prosthesis will have to be readjusted, or in some cases, a new mandibular prosthesis will need to be shaped, before the mandibular prosthesis can be implanted.

Another deficiency is the inability of these prior approachs to be easily and quickly modified, or customized, during surgery. Should the mandibular prosthesis be attached to the mandible when the fit is not precise, these prior approachs do not allow for easy modification and customization of the mandibular prosthesis. Accordingly, should unforeseen circumstances render the pre-formed prosthesis unworkable, a new prosthesis will be required, causing delay and increased surgery time. A new prosthesis may also be required should the physician find it necessary to remove more of the patient's mandible during the operation than was originally planned due to undetected spreading of the disease.

Accordingly, prior to the development of the present invention, there has been no mandibular 10 prosthesis which: allows for easy readjustment while the mandibular prosthesis is in place; allows easy modification due to unforeseen circumstances; obtains more accurate occlusion without planning in a single rapid step; eliminates plate bending; decreases operating time; and improves the shape of the mandibular prosthesis to reduce any damage which may be caused by the placement of the mandibular prosthesis. Therefore, the art has sought a mandibular prosthesis which: allows for easy readjustment while the mandibular prosthesis is in place; allows easy modification due to unforeseen circumstances; obtains more accurate occlusion without planning in a single rapid step; eliminates plate bending; decreases operating time; and improves the shape of the mandibular prosthesis to reduce any damage which may be caused by the placement of the mandibular prosthesis. It is believed that the present invention will achieve these objectives and overcome the disadvantages of other devices in the field of the invention, but its results or effects are still dependent upon the skill and training of the operator.

SUMMARY OF INVENTION

In accordance with the invention, the foregoing advantages have been achieved through the present mandibular prosthesis for use as a replacement of a portion of a patient's mandible. The mandibular prosthesis includes a pair of anchor plates, at least two assembly plates, and at least one link. Each anchor plate has first and second ends, the first end of each anchor plate including a first swivel member, and the second end of each anchor plate being adapted to be attached to a portion of the patient's mandible. The at least two assembly plates are disposed between the anchor plates. Each of the at least two assembly plates include first and second ends, the first and second ends of each of the at least two assembly plates each having a second swivel member. Each link includes first and second ends, the first and second ends of each link having a first swivel member. The at least one link is disposed between the at least two assembly plates with a first swivel member of the at least one link matingly engaged with an adjacent second swivel member of an assembly plate. The first swivel member of an anchor plate is matingly engaged with an adjacent second swivel member of an assembly plate. Each matingly engaged first and second swivel members define a swivel coupling which permits three dimensional movement between the first and second swivel members.

A further feature may the mandibular prosthesis is that each assembly plate may include a releasable locking member, such as a screw, to releasably lock each swivel coupling defined by each matingly engaged first and second swivel members. An additional feature of the mandibular prosthesis is that each of the at least two assembly plates may include two clamping plates. Another feature of the mandibular prosthesis is that each clamping plate may include an inner wall and an outer wall, the inner wall including the second swivel member. A further feature of the mandibular prosthesis is that the two clamping plates may include a releasable locking member, such as a screw, to releasably lock the two clamping plates. An additional feature of the mandibular prosthesis is that the first swivel member may be a ball and the second swivel member may be a recess formed by the inner wall, for mating engagement with the ball. Still another feature of the mandibular prosthesis is that the mandible has a lingual surface and a labial surface and the first swivel member of each anchor plate may lie in a plane which is disposed intermediate the lingual and labial surfaces of the mandible. A further feature of the mandibular prosthesis is that the mandible has a lingual surface and a labial surface and the first end of each anchor plate may include a flange extending toward the lingual surface of the mandible. An additional feature of the mandibular prosthesis is that each of the at least one first swivel members of each anchor plate may be disposed on the flange. Another feature of the mandibular prosthesis is that the mandible has a lingual surface and a labial surface and the swivel coupling defined by each matingly engaged first and second swivel members may be disposed intermediate the lingual surface and the labial surface. An additional feature of the mandibular prosthesis is that the first swivel member may be a ball and the second swivel member may be a recess for mating engagement with the ball.

In accordance with the invention, the foregoing advantages have also been achieved through the present modular mandibular prosthesis for use as a replacement of a portion of a patient's mandible. The mandibular prosthesis includes a pair of anchor plates, at least two links, and at least one assembly plate. Each anchor plate includes first and second ends, the first end of each anchor plate having a first swivel member, and the second end of each anchor plate being adapted to be attached to a portion of the patient's mandible. Each of the at least two links include first and second ends, the first and second ends of each of the at least two links having a second swivel member. Each assembly plate includes first and second ends, the first and second ends of each assembly plate having a first swivel member. The at least one assembly plate is disposed between each of the at least two links with a first swivel member of the at least one assembly plate matingly engaged with an adjacent second swivel member of a link. The first swivel member of an anchor plate is matingly engaged with an adjacent second swivel member of a link. Each matingly engaged first and second swivel members define a swivel coupling which permits three dimensional movement between the first and second swivel members.

A further feature of this embodiment is that the first swivel member may be a recess and the second swivel member may be a ball for mating engagement with the recess.

In accordance with the invention, the foregoing advantages have also been achieved through the present modular mandibular prosthesis for use as a replacement of a portion of a patient's mandible. The mandibular prosthesis includes a pair of anchor plates, at least two assembly plates, and at least one link. Each anchor plate includes first and second ends, the second end of each anchor plate being adapted to be attached to a portion of the patient's mandible. Each assembly plate includes two ends and each link includes two ends. The at least two assembly plates are disposed between the anchor plates and one end of an assembly plate is connected to the first end of an anchor plate thereby defining a connection. The two ends of the at least one link are connected to an adjacent assembly plate thereby defining a connection. Each connection between an anchor plate and an assembly plate and each connection between a link and an assembly plate defining a swivel coupling which permits three dimensional movement at each swivel coupling.

A further feature of the mandibular prosthesis is that each assembly plate may include a releasable locking member to releasably lock each swivel coupling to substantially prevent three dimensional movement after the releasable locking member is locked.

In accordance with the invention, the foregoing advantages have also been achieved through the present modular mandibular prosthesis for use as a replacement of a portion of a patient's mandible. The mandibular prosthesis includes a pair of anchor plates and at least one connector member. Each anchor plate includes first and second ends, the second end of each anchor plate being adapted to be attached to a portion of the patient's mandible. The at least one connector member includes first and second ends and is disposed between the anchor plates. The first end of a connector member is connected to the first end of one anchor plate thereby defining a connection, and the second end of a connector member is connected to the first end of the other anchor plate thereby defining a connection. Each connection defines a swivel coupling which permits three dimensional movement at each connection.

A further feature of the mandibular prosthesis is that the first end of at least one connector member may be connected to the second end of another connector member thereby defining a connection. An additional feature of the mandibular prosthesis is that the connecting member may be a link. Another feature of the mandibular prosthesis is that the connecting member may be an assembly plate. A further feature of the mandibular prosthesis is that the connecting member may be at least one integrated link-assembly plate. Still another feature of the mandibular prosthesis is that the first end of an integrated link-assembly plate is connected to the second end of an integrated link-assembly plate thereby defining a connection.

The modular mandibular prosthesis of the present invention, when compared with previously proposed prior mandibular prosthesis is believed to have the advantages of: allowing easy readjustment while the mandibular prosthesis is in place; allowing easy modification due to unforeseen circumstances; obtaining more accurate occlusion without planning in a single rapid step; eliminating plate bending; decreasing operating time; and improving the shape of the mandibular prosthesis to reduce any damage which may be caused by the placement of the mandibular prosthesis. It is believed that the present invention will achieve these objectives and overcome the disadvantages of other devices in the field of the invention, but its results or effects are still dependent upon the skill and training of the operator.

BRIEF DESCRIPTION OF DRAWINGS

FIG. 2 is a perspective view of one embodiment of the anchor plate used in connection with the specific embodiment of FIG. 1.

FIG. 3 is a top view of one embodiment of the link used in connection with the specific embodiment of FIG. 1.

FIG. 4 is a front view of the inner wall of a clamping plate used in connection with the specific embodiment of FIG. 1.

FIG. 5 is a front view of the outer wall of the clamping plate in FIG. 4 used in connection with the specific embodiment of FIG. 1.

FIG. 7 is a cross-sectional view of a preferred embodiment of the assembly plate.

FIG. 8 is a perspective view of one embodiment of the integrated link-assembly plate used in connection with one specific embodiment of the modular mandibular prosthesis of the present invention.

FIG. 9 is a perspective view of the embodiment of FIG. 1 during occlusion of the teeth of the mandible with the teeth of the maxilla of a human being.

Figure 6:
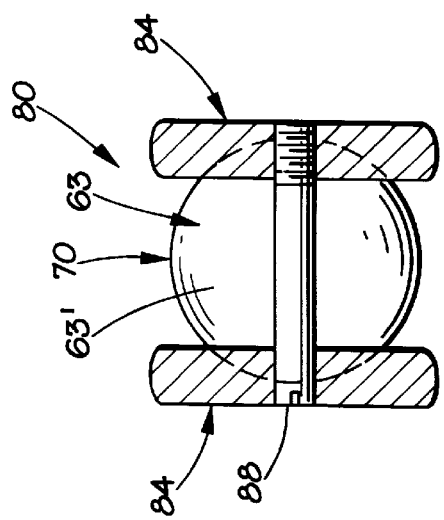
FIG. 6 is a cross-sectional view along line 6—6 in FIG. 1 of the assembly plate used in connection with the specific embodiment of FIG. 1.

While the invention will be described in connection with the preferred embodiments, it will be understood that it is not intended to limit the invention to those embodiments. On the contrary, it is intended to cover all alternatives, modifications, and equivalents, as may be included within the spirit and scope of the invention as defined by the appended claims.

DETAILED DESCRIPTION AND SPECIFIC EMBODIMENTS

The present invention relates to a modular mandibular prosthesis, or mandibular prosthesis, used as a replacement for a portion of a patient's mandible, or lower jaw, which has been surgically removed due to disease, such as cancer. In a broad aspect of the invention, the mandibular prosthesis includes a pair of anchor plates and at least one connector member. As will be discussed in greater detail below, the anchor plates are attached to the remaining portion of the mandible. At least one connector member is then connected to the anchor plates, and to other connector members if necessary or desired, thereby defining a connection, to form a mandibular prosthesis which is attached to the remaining portion of the mandible by the anchor plates. Each connection formed between the anchor plate and a connector member, or between adjacent connector members, defines a swivel coupling which permits three dimensional movement at the connection as will be hereinafter described in greater detail. It is to be understood that any type of connector member or anchor member may be employed to form the modular mandibular prosthesis of the invention provided the connections define swivel couplings which permit three-dimensional, or multiplanar, movement at the connections. For example, as will be described below in greater detail, the connector member may be a link, an assembly plate, or an integrated link-assembly plate.

In one specific embodiment, the mandibular prosthesis may include at least one link, each link having at least a first end and a second end, disposed between at least two assembly plates. The at least two assembly plates are connected to the anchor plates as described above to form the swivel couplings. The first end of at least one link may then be connected to the second end of an assembly plate to form a swivel coupling, and the second end of the link may be connected to the first end of an assembly plate to form a swivel coupling. The first end of another link may then be connected to the first end of an assembly plate to form a swivel coupling, and the second end of the link may be connected to the first end of an assembly plate to form a swivel coupling. This arrangement may be continued to construct a modular mandibular prosthesis having the desired, or necessary, length. Each swivel coupling preferably permits three dimensional movement of each assembly plate or link with respect to at least one adjacent anchor plate, link, or assembly plate. As discussed in greater detail below, the three dimensional movement facilitates implantation in the proper orientation. After the modular mandibular prosthesis is properly orientated, a releasable locking member may be used to secure each connection in the proper orientation.

Figure 1:
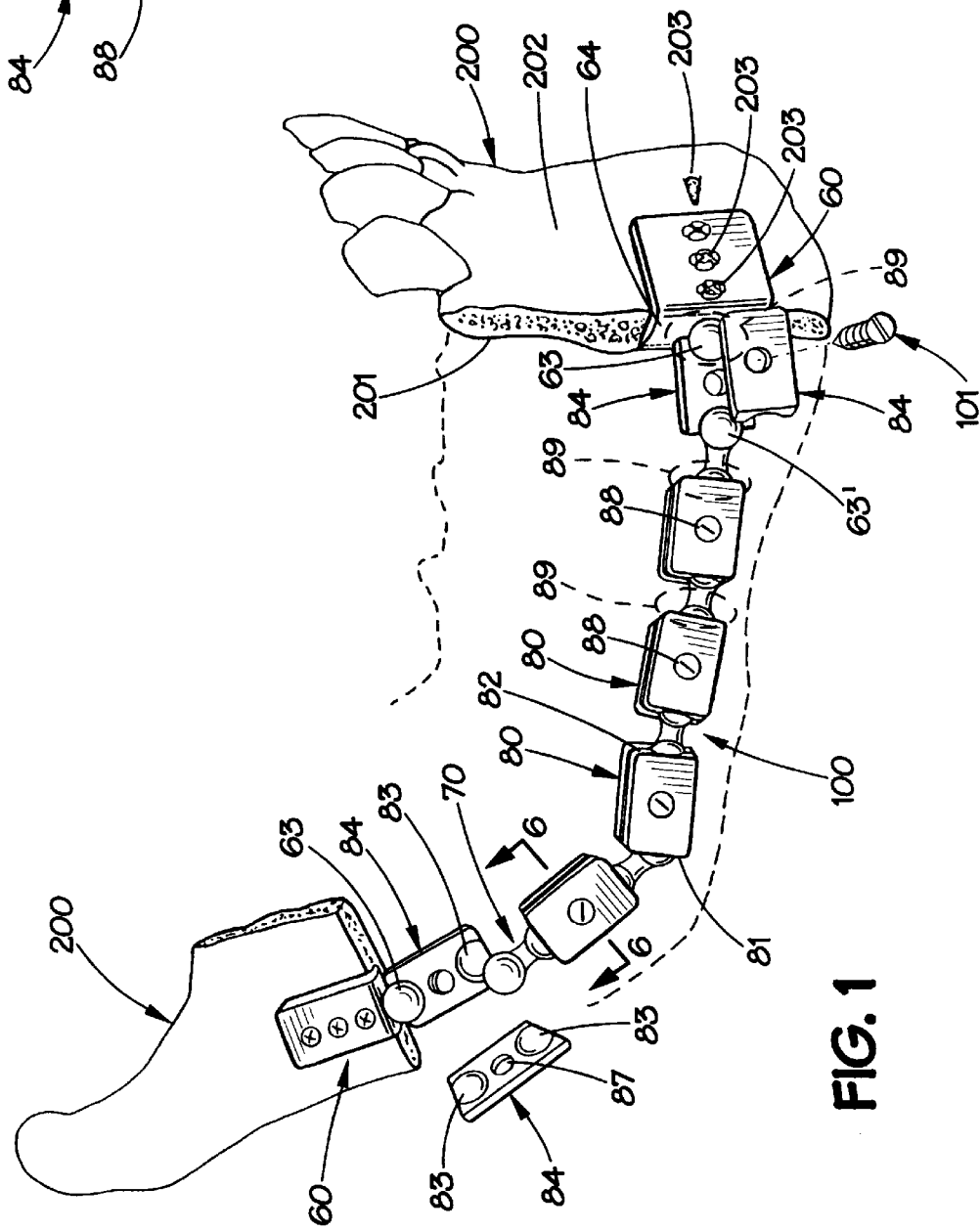
FIG. 1 is a perspective view of one specific embodiment of the modular mandibular prosthesis of the present invention as placed in the mandible of a human being.

Referring now to the drawings, wherein like numerals denote identical elements throughout the several views and primed reference numerals denote elements having a similar structure and function to those elements having the same unprimed reference numeral, FIGS. 1–10 show specific embodiments of the present invention. As shown in FIG. 1, in one specific embodiment of the invention, a modular mandibular prosthesis 100 for use after the resection of a patient's mandible 200 includes a pair of anchor plates 60, at least one link 70, at least two assembly plates 80, and at least one releasable securing member 88. In this specific embodiment, and as will be discussed below in further detail, an assembly plate 80 is connected to each anchor plate 60 thereby defining a connection. A link 70 is connected to two assembly plates 80 thereby defining a connection between a link 70 and two assembly plates 80. Each connection defines a swivel coupling 89 which permits three dimensional movement at each connection.

Referring now to FIG. 2, each anchor plate 60 includes a first end 61, a second end 62 and a first swivel member 63 disposed proximate the first end 61. Preferably, the first swivel member 63 is incorporated into the first end 61 of each anchor plate 60. The second end 62 of the anchor plate 60 is adapted to be attached to a portion of the patient's mandible 200. As illustrated in FIG. 1, the mandible 200 includes a lingual surface 201 and a labial surface 202. The first end 61 of each anchor plate 60 may include a flange 64 angularly disposed with respect to the anchor plate 60 and extending toward the lingual surface 201 of the patient's mandible 200. The flange 64 is preferably disposed at an angle 65 with respect to the anchor plate 60, angle 65 is about equal to the angle of the cut made by the physician when removing the diseased portion of the mandible 200. Preferably, the cut made by the physician is at an angle of about 90 degrees, or perpendicular, to the remaining portion of the mandible 200, and thus, the anchor plate 60 and the flange 64 are angularly disposed with respect to one another at an angle of about 90 degrees. In this specific embodiment, the first swivel member 63 is incorporated into the flange 64, as by forming the first swivel member 63 integral with flange 64 such that the first swivel member 63 of each anchor plate 60 lies in a plane which is disposed intermediate the lingual surface 201 and the labial surface 202 of the patient's mandible 200. Alternatively, if desired, the first swivel member 63 may be associated with the first end 61, or flange 64, of anchor plate 60, as by glue, epoxy, welding, or a threaded connector. It is contemplated that this orientation enhances the ability of the modular mandibular prothesis 100 to be properly orientated across the gap formed by the removed or injured of a portion of the mandible 200.

Each anchor plate 60 may be secured to the mandible by any method known to persons skilled in the art. Preferably, each anchor plate 60 includes at least one attachment hole 66. As shown in FIG. 1, each anchor plate 60 preferably includes three attachment holes 66. In this preferred embodiment, each anchor plate 60 is secured to the mandible 200 by inserting screws, such as hollow titanium screws 203 known in the art, through each attachment hole 66, and into the mandible 200.

Still with reference to FIG. 1, this specific embodiment includes at least one link 70, shown in detail in FIG. 3, disposed between the at least two assembly plates 60. Each link 70 increases the length of the modular mandibular prosthesis 100 to facilitate formation of the mandibular prosthesis across varying gaps in the mandible 200 created by resection of a portion of the mandible 200. Accordingly, the modular mandible prosthesis 100 can be adjusted by the addition or subtraction of one or more links 70, which in turn requires the addition of one or more assembly plates 80.

As shown in FIG. 3, each link 70 includes a first end 71 and a second end 72. Both the first end 71 and the second end 72 of each link 70 include a first swivel member 63'. The first swivel member 63' at first end 71 of the link 70 is connected to the first swivel member 63' at the second end 72 of the link 70 by a bridge 74. Preferably, the thickness of bridge 74 is less than that of the first swivel member 63'.

Still with reference to FIG. 1, this specific embodiment includes at least two assembly plates 80 disposed between the pair of anchor plates 60. Each assembly plate 80 may include two clamping plates 84 as shown in FIGS. 4–5 and will be hereinafter described in grater detail. Each assembly plate 80 includes a first end 81 and a second end 82. The first end 81 and the second end 82 each 25 include a second swivel member 83. Each assembly plate 80 may also include at least one assembly hole 87 to facilitate securing each assembly plate 80 to each first swivel member 63, 63'. Preferably, each assembly plate 80 includes one assembly hole 87. Each assembly hole 87 is designed such that a releasable locking member 88 may be placed through the assembly hole 87 to secure the assembly plate 80 to the first swivel member 63, 63' to form the swivel coupling 89. The releasable locking member 88 should be designed such that the assembly plate 80 may be secured to the first swivel member 63, 63' to prevent the connection between the assembly plate 80 and the first swivel member 63, 63' from separating, however, each connection should provide multiplanar movement of the first swivel member 63, 63' and the assembly plate 80 at each swivel coupling 89. Preferably, each swivel coupling 89 defined by each matingly engaged first swivel member 63, 63' and second swivel member 83 is intermediate the lingual surface 201 and the labial surface 202 of the mandible 200.

After the modular mandibular prosthesis 100 is properly oriented, which is facilitated by allowing multiplanar movement of the first swivel member 63, 63' and the assembly plate 80 at the swivel coupling 89, the releasable locking member 88 may then be tightened to secure the first swivel member 63, 63' and the assembly plate 80 such that the modular mandibular prosthesis 100 is rigid and multiplanar movement at each swivel coupling 89 is no longer possible. Preferably, the releasable locking member 88 is a screw as shown in FIG. 1, threadedly received in assembly hole 87.

Each first swivel member 63, 63' and second swivel member 83 may have any geometrical shape suitable to provide multiplanar, or three dimensional, movement of each link 70 or assembly plate 80 to facilitate placing the modular mandibular prosthesis 100 in the proper orientation. After each link 70 and assembly plate 80 are placed in the desired position, the assembly plate 80 may be secured to each first swivel member 63, 63' using the releasably locking member 88 to maintain the desired orientation. Preferably, each first swivel member 63, 63' is spherical, i.e., ball shaped.

The second swivel member 83 preferably has a contour which is reciprocal, or mates, to the shape of each first swivel member 63, 63' to facilitate securing each first swivel member 63, 63' to each second swivel member 83. Preferably, each second swivel member 83 is a recess 83' having a contour which is concave to reciprocate the preferred shaped of each first swivel member 63, 63', namely, spherical. It is contemplated, however, that the first swivel member 63, 63' and the second swivel member 83 may be any shape which, provides a swivel coupling 89 which permits three dimensional movement at the swivel coupling 89. Furthermore, as discussed below in other specific embodiments, the first swivel member 63, 63' may be a recess and the second swivel member 83 may be spherical, i.e. a ball.

As further illustrated in FIGS. 4–5, each assembly plate 80 may include two clamping plates 84 having an inner wall 85, and an outer wall 86. The inner wall 85 of each assembly plate 80 may include the second swivel members 83, or recesses 83'. Each clamping plate 84 may also include an assembly hole 87. The releasable locking member 88 may then be placed through the assembly hole 87 to secure at least two clamping plates 84 in the same manner as described above. Preferably, the releasable locking member 88 is a screw 101 as shown in FIG. 1. The two clamping plates 84 are secured to one another such that the second swivel member 83 of the inner wall 85 of each clamping plate 84 is in contact with each first swivel member 63, 63'. Preferably, each first swivel member 63 of each anchor plate 60 and first swivel member 63' of each link 70 utilized in the modular mandibular prothesis 100 are disposed between the inner wall 84 of each clamping plate 84 such that each second swivel member 83 of the inner wall 85 is in contact with each first swivel member 63, 63'.

Each assembly plate 80, and accordingly each clamping plate 84, may be shaped in any geometrical shape suitable to replace the portion of the mandible which has been removed. Preferably, each assembly plate 80 should be shaped such that no sharp edges remain which may cause damage and/or pain to the patient, e.g., the corners are rounded. Accordingly, each assembly plate 80 should have the cross-section shown in FIG. 6. As further illustrated in FIG. 7, each assembly plate 80 may have a cross-section which is substantially circular.

As discussed above, the releasable locking member 88 should provide attachment of each clamping plate 84 such that each first swivel member 63, 63' is disposed between the clamping plates 84 such that each first swivel member 63, 63' can not be removed from between the two clamping plates 84. The releasable locking member 88 should, however, be adjustable such that the connections between each first swivel member 63, 63' and each clamping plate 84 are allowed to flex along the length of the modular mandibular prosthesis 100 by permitting three dimensional movement at each of the connections, or swivel couplings 89. After the modular mandibular prosthesis 100 is placed in its proper orientation, each releasable locking member 88 is tightened to prevent multiplanar movement, thus rendering the entire length of the modular mandibular prosthesis 100 rigid.

Referring now to FIG. 8, in another specific embodiment of the invention, the connector member is an integrated link-assembly member 90. The integrated link-assembly member 90 includes a first end 91 and a second end 92. The first end 91 includes a first swivel member 93 and the second end includes a second swivel member 94 which is designed to reciprocate the shape of the first swivel member 93 as described in greater detail above. In this specific embodiment, the first swivel member 93 and the second swivel member 94 engage one another to form a swivel coupling (not shown) which permits three dimensional movement at the swivel coupling. The first swivel member 93 of an integrated link-assembly plate 90 engages a second swivel member 94 of an anchor plate 60 and a second swivel member 94 of an integrated link-assembly plate 90 engages a first swivel member 93 of another anchor plate 60. In this specific embodiment one anchor plate 60 may have a first swivel member 93 and the other anchor plate 60 may have a second swivel member 94. The integrated link-assembly plate 90 may include an assembly hole 95 to enhance the ability of the integrated link-assembly plate 90 to secure the matingly engagement between the first swivel member 93 and the second swivel member 94. Each integrated link-assembly plate 90 may also include at least one releasable locking member 88 inserted through assembly hole 95 to secure the swivel couplings.

As further described above, the first swivel member 93 and the second swivel member 94 may have any shape which provides a swivel coupling. Preferably, the swivel coupling is defined at each connection between an anchor plate 60 and an integrated link-assembly plate 90 or between adjacent integrated link-assembly plates 90. Each swivel coupling preferably permits three dimensional movement of each integrated link-assembly plate 90 with respect to an adjacent anchor plate 60 or an adjacent link-assembly plate 90.

In another specific embodiment of the invention utilizing the integrated link-assembly member 90 described above, the modular mandibular prosthesis may include a link 70 as described above, or an assembly plate 80, as described above, to connect an integrated link-assembly plate 90 to one of the anchor plates 60. In this specific embodiment, both anchor plates include either a first swivel member 63 as shown in FIG. 1–2 which is identical to first swivel member 93, or a second swivel member 94 which reciprocates the shape of the first swivel member 93. In other words, the pair of anchor plates are identical.

In another specific embodiment, the modular mandibular prosthesis may include a pair of anchor plates 60 as shown in FIG. 2 and described above, and one assembly plate 80 as shown in FIGS. 1, 4–5. The assembly plate 80 is disposed between the anchor plates 60 such that the first swivel member 63 of each anchor plate 60 is matingly engaged with an adjacent second swivel member 83 of the assembly plate 80. Each matingly engaged first swivel member 63 and second swivel member 83 define a swivel coupling 89 which permits three dimensional movement of the assembly plate 80 with respect to an adjacent anchor plate 60. In this embodiment, the first swivel coupling 63 is preferably a ball, as shown in FIGS. 1–2, and the second swivel coupling 83 is preferably a recess 83', as shown in FIGS. 1, 4–5, for mating engagement with the ball.

In other specific embodiments, the first swivel member and second swivel member may be designed to alter the minimum number of assembly plates or links. For example, as shown in FIG. 9, the anchor plate 400 may include a first swivel member 410, an assembly hole 420, and three attachment holes 430. As further shown in FIG. 9, the first swivel member 410 of the anchor plate 400 may be a recess 410'. In such an embodiment, the mandibular prosthesis may be formed using one link 70 as described above and shown in FIG. 3, or at least two links 70 and at least one assembly plate 80 as described above and shown in FIGS. 1, 4–5. A releaseably locking member 88 as described above, may be inserted through assembly hole 420 to secure the connection between the first swivel member 410, 410' and a second swivel member 63, 63' of a link 70. In this embodiment, as in the embodiments described above, each connection formed between an anchor plate 400 and a link 70 or a link 70 and an assembly plate 80 permits three dimensional movement at the connections.

The anchor plates 60, link 70, assembly plates 80, releasable securing members 88, and integrated link-assembly plate 90 may all be constructed out of any material having the desired strength and durability characteristics suitable for implantation into an animal or human. For example, stainless steel or titanium may be used. Preferably, all of the individual components of the modular mandibular prosthesis are constructed out of titanium. The anchor plates 60, link 70, assembly plates 80, releasable securing members 88, and integrated link-assembly plate 90 may also be have a plasma coating, or other chemical coating which enhances the connection between the various components and/or facilitates growth of bone across the surface of the components.

The flexibility along the modular mandibular prosthesis and the multiplanar movement of each connection between each the anchor plates and adjacent connector members or each connector member provide easy and quick installation and customization of the mandibular prosthesis. By simply adding or removing links, assembly plates, and/or integrated link-assembly plates as necessary or desired, the physician can increase or decrease the length of the mandibular prosthesis to the length required to replace the portion of the mandible which has been surgically removed. Customization of the modular mandibular prosthesis in this manner is very simple and can be accomplished quickly during the implantation surgical procedure.

Figure 10:
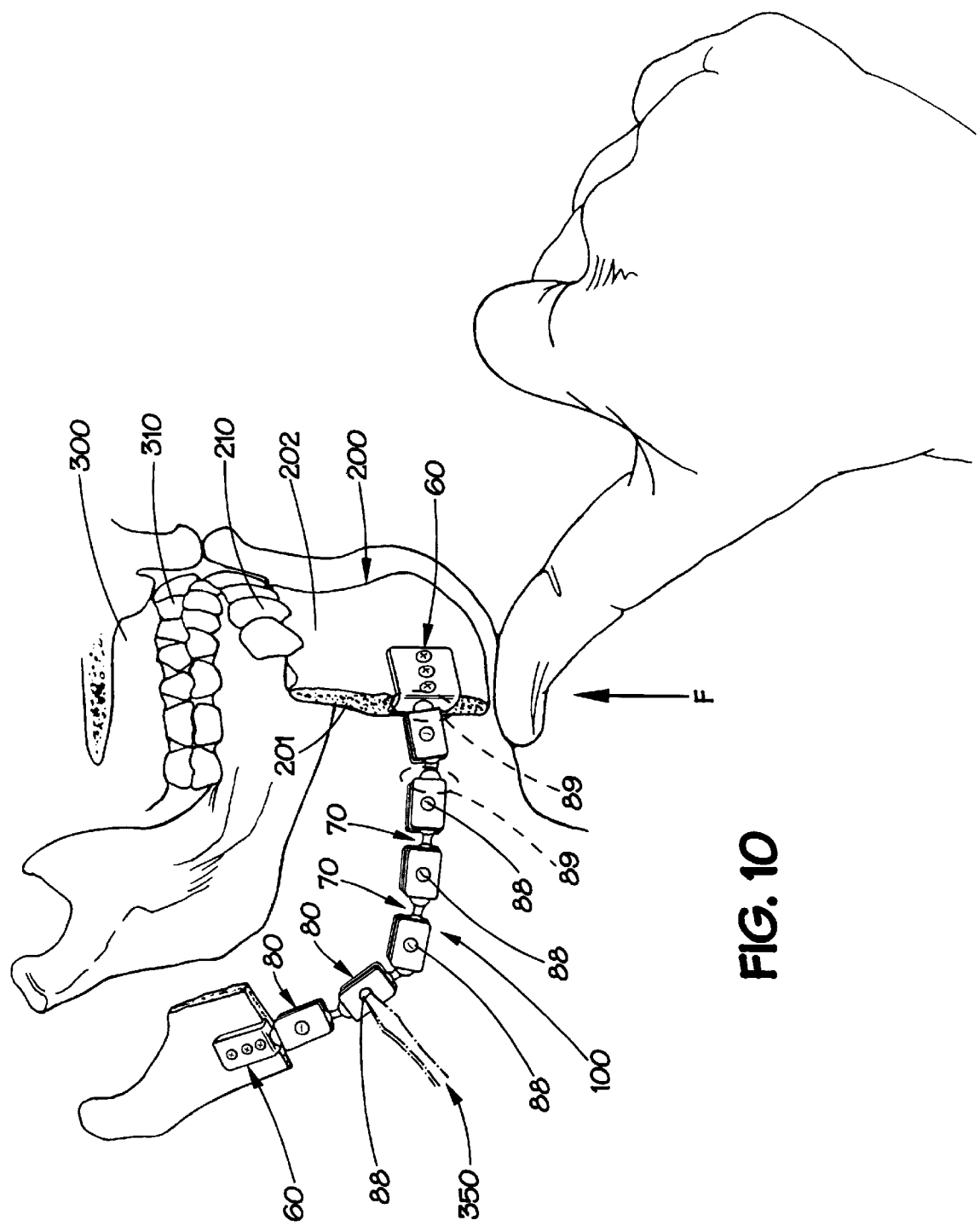
FIG. 10 is a cross-sectional view of one embodiment of an anchor plate.

Referring now to FIG. 10, the flexibility and multiplanar movement also provide easy occlusion between the teeth of the mandible and maxilla. After implantation, but before the releasable locking members 88 are tightened to prevent multiplanar movement, the physician can apply a small amount of force to the mandible 200 in an upward direction F to align the teeth 210 of the mandible 200 with the teeth 310 of the maxilla 300. The flexibility and multiplanar movement of the modular mandibular prosthesis 100 allow the modular mandibular prosthesis 100 to shift in concert with the movement of the mandible 200 during the alignment of the teeth, thereby facilitating the proper orientation of the modular mandibular prosthesis 100 to replace the portion of the mandible removed or injured. During the occlusion of the teeth, the flexibility and multiplanar movement of the modular mandibular prosthesis 100 allows each link 70, assembly plate 80 or integrated link-assembly plate 90 to shift, or "buckle" in any direction required for the modular mandibular prosthesis 100 to achieve its proper orientation. Preferably, each connection, or swivel coupling 89, is disposed intermediate the lingual surface 201 of the mandible 200 and the labial surface 202 of the mandible 200. After the physician has aligned the teeth, and modular mandibular prosthesis 100 is in its desired orientation, the releasable locking members 88 may then be tightened, using a screw driver 350 for example, to permanently fix each link 70, assembly plate 80, or integrated link-assembly plate 90 in the desired orientation. Accordingly, the modular mandibular prosthesis 100 is no longer capable of multiplanar movement at the connections or swivel couplings 89.

It is to be understood that the invention is not limited to the exact details of construction, operation, exact materials, or embodiments shown and described, as obvious modifications and equivalents will be apparent to one skilled in the art. For example, any number or combination or links, assembly plates or integrated link-assembly plates may be used to form the modular mandibular prosthesis. Further, any type of first swivel coupling or second swivel coupling may be used provided the connection between each first swivel coupling and second swivel coupling defines a swivel coupling which provides three dimensional movement of the link, assembly plate or integrated link-assembly plate at the swivel coupling. Also, any type of releasable locking member may be used in connection with each assembly plate, integrated link-assembly plate or anchor plate provided that the releasable locking member allows the modular mandibular prosthesis to flexibly connect to facilitate orientation of the modular mandibular prosthesis prior to tightening, or locking, the releasable locking member thereby securing the modular mandibular prosthesis in its desired orientation. Accordingly, the invention is therefore to be limited only by the scope of the appended claims.

What is claimed is:

1. A mandibular prosthesis, for use as a replacement of a portion of a patient's mandible, comprising:
   a pair of anchor plates, each anchor plate having first and second ends, the first end of each anchor plate having a first swivel member, and the second end of each anchor plate adapted to be attached to a portion of the patient's mandible;

at least two assembly plates disposed between the anchor plates, each of the at least two assembly plates having first and second ends, the first and second ends of each of the at least two assembly plates each having a second swivel member;

at least one link, each link having first and second ends, the first and second ends of each link having a first swivel member;

the at least one link being disposed between the at least two assembly plates, with a first swivel member of the at least one link matingly engaged with an adjacent second swivel member of an assembly plate;

the first swivel member of an anchor plate being matingly engaged with an adjacent second swivel member of an assembly plate; and each matingly engaged first and second swivel members defining a swivel coupling which permits three dimensional movement between the first and second swivel members.

2. The mandibular prosthesis of claim 1, wherein each assembly plate includes a releasable locking member to releasably lock each swivel coupling defined by each matingly engaged first and second swivel members.

3. The mandibular prothesis of claim 2, wherein the releasable locking member is a screw.

4. The mandibular prosthesis of claim 1, wherein each of the at least two assembly plates include two clamping plates.

5. The mandibular prosthesis of claim 4, wherein each clamping plate includes an inner wall and an outer wall, the inner wall including the second swivel member.

6. The mandibular prosthesis of claim 5, wherein the two clamping plates include a releasable locking member to releasably lock the two clamping plates.

7. The mandibular prosthesis of claim 6, wherein the releasable locking member is a screw.

8. The mandibular prosthesis of claim 7, wherein the first swivel member is a ball and the second swivel member is a recess formed by the inner wall, for mating engagement with the ball.

9. The mandibular prosthesis of claim 1, wherein the mandible has a lingual surface and a labial surface and the first swivel member of each anchor plate lies in a plane which is disposed intermediate the lingual and labial surfaces of the mandible.

10. The mandibular prosthesis of claim 1, wherein the mandible has a lingual surface and a labial surface and the first end of each anchor plate includes a flange extending toward the lingual surface of the mandible.

11. The mandibular prosthesis of claim 10, wherein each of the at least one first swivel members of each anchor plate is disposed on the flange.

12. The mandibular prosthesis of claim 1, wherein the mandible has a lingual surface and a labial surface and the swivel coupling defined by each matingly engaged first and second swivel member is disposed intermediate the lingual surface and the labial surface.

13. The mandibular prosthesis of claim 1, wherein the first swivel member is a ball and the second swivel member is a recess for mating engagement with the ball.

14. A mandibular prosthesis, for use as a replacement of a portion of a patient's mandible, comprising:

a pair of anchor plates, each anchor plate having first and second ends, the first end of each anchor plate having a first swivel member, and the second end of each anchor plate adapted to be attached to a portion of the patient's mandible;

at least two links disposed between the anchor plates, each of the at least two links having first and second ends, the first and second ends of each of the at least two links having a second swivel member;

at least one assembly plate, each assembly plate having first and second ends, the first and second ends of each assembly plate having a first swivel member;

the at least one assembly plate being disposed between each of the at least two links, with a first swivel member of the at least one assembly plate matingly engaged with an adjacent second swivel member of a link;

the first swivel member of an anchor plate being matingly engaged with an adjacent second swivel member of a link; and each matingly engaged first and second swivel members defining a swivel coupling which permits three dimensional movement between the first and second swivel members.

15. The mandibular prosthesis of claim 14, wherein the first swivel member is a recess and the second swivel member is a ball for mating engagement with the recess.

16. A mandibular prosthesis, for use as a replacement of a portion of a patient's mandible, comprising:

a pair of anchor plates, each anchor plate having first and second ends, the second end of each anchor plate adapted to be attached to a portion of the patient's mandible;

at least two assembly plates disposed between the anchor plates, each of the at least two assembly plates having two ends;

at least one link, each link having two ends;

one end of an assembly plate being connected to the first end of an anchor plate thereby defining a connection;

the two ends of the at least one link being connected to an adjacent assembly plate thereby defining a connection; and each connection between an anchor plate and an assembly plate and each connection between a link and an assembly plate defining a swivel coupling which permits three dimensional movement at each swivel coupling.

17. The mandibular prosthesis of claim 16, wherein each assembly plate includes a releasable locking member to releasably lock each swivel coupling to substantially prevent three dimensional movement after the releasable locking member is locked.

18. A mandibular prosthesis, for use as a replacement of a portion of a patient's mandible, comprising:

a pair of anchor plates, each anchor plate having first and second ends, the second end of each anchor plate adapted to be attached to a portion of the patient's mandible;

at least one connector member disposed between the anchor plates, the at least one connector having first and second ends;

the first end of a connector member being connected to the first end of one anchor plate thereby defining a connection;

the second end of a connector member being connected to the first end of the other anchor plate thereby defining a connection; and each connection defining a swivel coupling which permits three dimensional movement at each connection.

19. The mandibular prosthesis of claim 18, wherein the first end of at leash one connector member is connected to the second end of another connector member thereby defining a connection.

20. The mandibular prosthesis of claim 18, wherein the connecting member is a link.

21. The mandibular prosthesis of claim 18, wherein the connecting member is an assembly plate.

22. The mandibular prosthesis of claim 18, wherein the connecting member is at least one integrated link-assembly plate.

23. The mandibular prosthesis of claim 22, wherein the first end of an integrated link-assembly plate is connected to the second end of an integrated link-assembly plate thereby defining a connection.

* * * * *